United States Patent
Kamimura et al.

(10) Patent No.: US 7,057,389 B2
(45) Date of Patent: Jun. 6, 2006

(54) NUCLEAR MAGNETIC RESONANCE DIAGNOSING DEVICE AND DIAGNOSING SYSTEM

(75) Inventors: Seiji Kamimura, Kodaira (JP); Ryosuke Fukami, Kokubunji (JP); Isamu Takekoshi, Tokyo (JP); Masakatsu Iwasaki, Sayama (JP); Hitoshi Yoshino, Kashiwa (JP); Tsuneo Maeda, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 6 days.

(21) Appl. No.: 10/481,641

(22) PCT Filed: Jun. 17, 2002

(86) PCT No.: PCT/JP02/06029

§ 371 (c)(1),
(2), (4) Date: Dec. 22, 2003

(87) PCT Pub. No.: WO03/001999

PCT Pub. Date: Jan. 9, 2003

(65) Prior Publication Data

US 2004/0232916 A1     Nov. 25, 2004

(30) Foreign Application Priority Data

Jun. 28, 2001  (JP) .............................. 2001-196528

(51) Int. Cl.
 *G01V 3/00* (2006.01)
 *A61B 5/055* (2006.01)
 *G01N 23/04* (2006.01)

(52) U.S. Cl. ...................... 324/318; 600/411; 600/427; 378/63; 324/319

(58) Field of Classification Search ........ 324/318–322; 5/601, 600; 378/63; 600/427, 411
See application file for complete search history.

(56) References Cited

U.S. PATENT DOCUMENTS

| 4,968,937 | A | * | 11/1990 | Akgun | 324/318 |
|---|---|---|---|---|---|
| 5,615,430 | A | * | 4/1997 | Nambe et al. | 5/600 |
| 5,713,357 | A | * | 2/1998 | Meulenbrugge et al. | 600/411 |
| 5,807,254 | A | * | 9/1998 | Meulenbrugge et al. | 600/411 |
| 5,818,901 | A | * | 10/1998 | Schulz | 378/63 |
| 5,864,236 | A | | 1/1999 | Li | 324/320 |
| 6,049,208 | A | | 4/2000 | Takekoshi et al. | 324/319 |

(Continued)

FOREIGN PATENT DOCUMENTS

GB     2355799 A  *  5/2001

(Continued)

*Primary Examiner*—Diego Gutierrez
*Assistant Examiner*—Tiffany A. Fetzner
(74) *Attorney, Agent, or Firm*—Reed Smith LLP; Stanley P. Fisher, Esq.; Juan Carlos A. Marquez, Esq.

(57) ABSTRACT

A nuclear magnetic resonance diagnosing apparatus for continuously taking tomograms in a space formed between a pair of magnets includes a cylindrical table top support of a gantry side, a pair of magnets vertically arranged, a table top support of the gantry side being interposed between the pair of magnets; and a column for supporting at least the magnet arranged in an upper side between the pair of magnets. The column is formed so that between a gantry and an examining table body, a width between a bridge construction, which is provided between the column and the table top support of the gantry side, and the table top support of the gantry side may be smaller than an examination width L determined by lines R' passing through a center of the table top support of the gantry side perpendicular to a center line R.

20 Claims, 12 Drawing Sheets

U.S. PATENT DOCUMENTS

| | | | |
|---|---|---|---|
| 6,101,239 A * | 8/2000 | Kawasaki et al. | 378/63 |
| 6,198,957 B1 * | 3/2001 | Green | 600/411 |
| 6,246,239 B1 * | 6/2001 | Krogmann et al. | 324/318 |
| 6,249,695 B1 * | 6/2001 | Damadian | 600/427 |
| 6,263,043 B1 * | 7/2001 | Maschke | 378/63 |
| 6,335,623 B1 * | 1/2002 | Damadian et al. | 324/320 |
| 6,366,798 B1 * | 4/2002 | Green | 600/411 |
| 6,385,480 B1 * | 5/2002 | Bachus et al. | 600/411 |
| 6,591,127 B1 * | 7/2003 | McKinnon | 600/411 |
| 6,658,085 B1 * | 12/2003 | Sklebitz | 378/63 |
| 2003/0110564 A1 * | 6/2003 | Yoshino et al. | 5/601 |
| 2003/0181808 A1 * | 9/2003 | McKinnon | 600/411 |
| 2004/0162480 A1 * | 8/2004 | Satragno et al. | 600/415 |
| 2004/0232916 A1 * | 11/2004 | Kamimura et al. | 324/318 |

FOREIGN PATENT DOCUMENTS

| | | |
|---|---|---|
| JP | 58-19240 | 7/1981 |
| JP | 58-19240 | 2/1983 |
| JP | 964036 | 7/1994 |
| JP | 2774777 | 11/1994 |
| JP | 3219389 | 11/1994 |
| JP | 9-266893 | 4/1996 |
| JP | 9-299352 | 5/1996 |
| JP | 08-140958 | 6/1996 |
| JP | 964036 | 9/1996 |
| JP | 1033071 | 6/1997 |
| JP | 10-127604 | 7/1997 |
| JP | 11-28199 | 7/1997 |
| JP | 9-266893 | 10/1997 |
| JP | 11-104109 | 10/1997 |
| JP | 9-299352 | 11/1997 |
| JP | 10-127604 | 5/1998 |
| JP | 2774777 | 7/1998 |
| JP | 11-188018 | 9/1998 |
| JP | 1068163 | 12/1998 |
| JP | 11-28199 | 2/1999 |
| JP | 1033071 | 2/1999 |
| JP | 11-104109 | 4/1999 |
| JP | 11-188018 | 7/1999 |
| JP | 1093585 | 12/1999 |
| JP | 2002-17708 | 7/2000 |
| JP | 1093585 | 12/2000 |
| JP | 1068163 | 2/2001 |
| JP | 1141648 | 4/2001 |
| JP | 3219389 | 10/2001 |
| JP | 11-56185 | 12/2001 |
| JP | 2002-17708 | 1/2002 |
| JP | 1172124 | 3/2002 |
| JP | 1172330 | 3/2002 |
| JP | 1172331 | 3/2002 |
| JP | 1141648 | 5/2002 |
| JP | 11-56185 | 10/2002 |
| JP | 1172124 | 4/2003 |
| JP | 1172330 | 4/2003 |
| JP | 1172331 | 4/2003 |
| WO | WO 200131358 A1 * | 5/2001 |

* cited by examiner

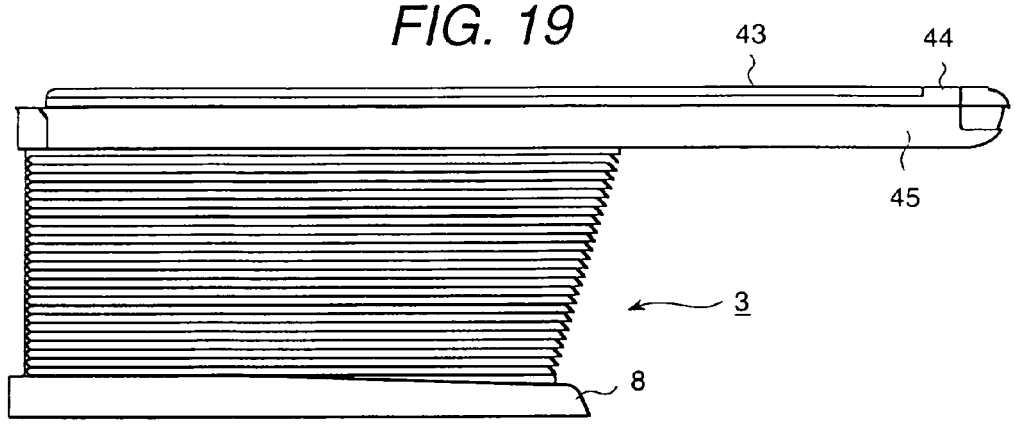
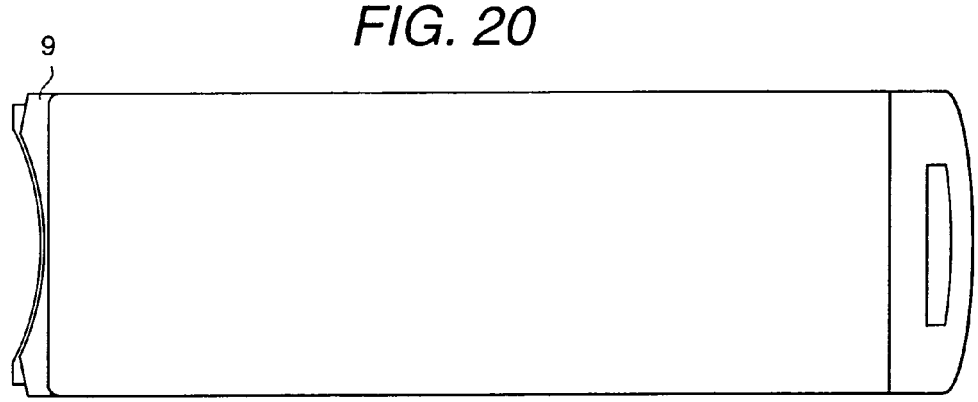

FIG. 23
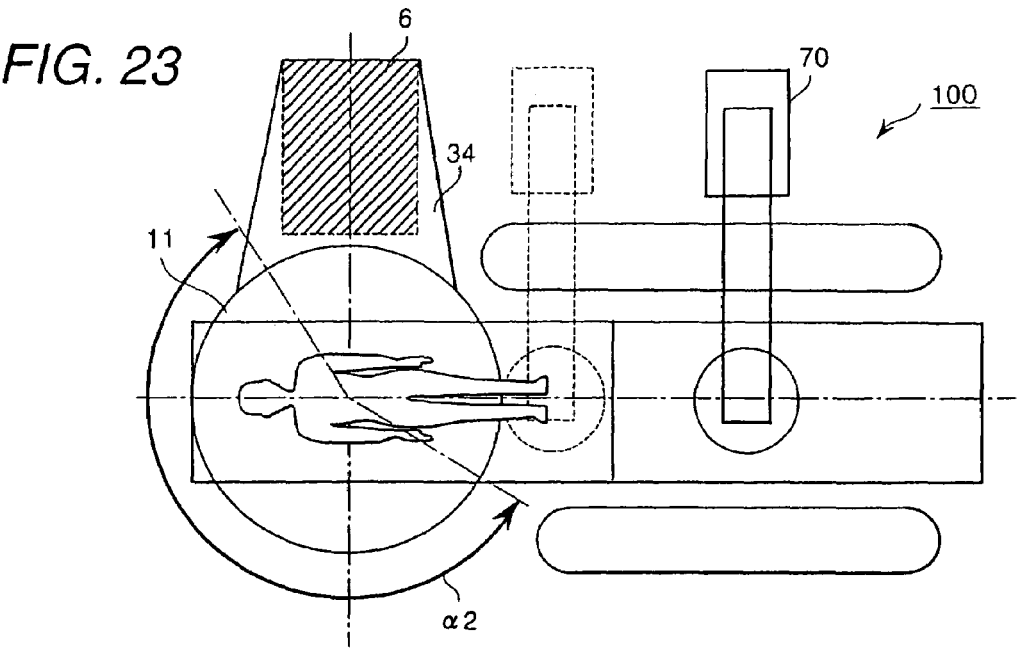
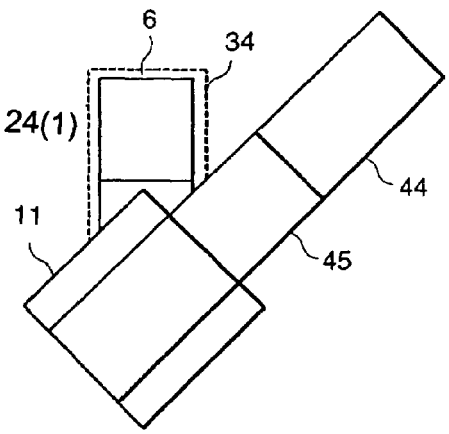
(1) TETRAGONAL TYPE
(THE ANGLE BETWEEN A BED
AND A GANTRY IS 45 DEGREES)
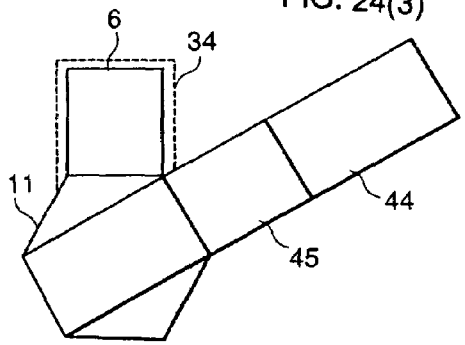
(3) HEXAGONAL TYPE
(THE ANGLE BETWEEN A BED
AND A GANTRY IS 60 DEGREES)
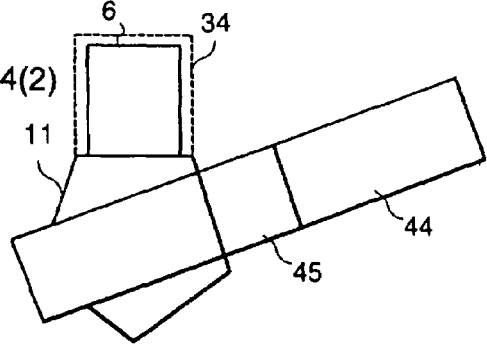
(2) PENTAGONAL TYPE
(THE ANGLE BETWEEN A BED
AND A GANTRY IS 72 DEGREES)
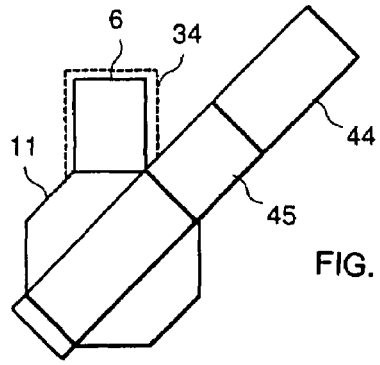
(4) OCTAGONAL TYPE
(THE ANGLE BETWEEN A BED
AND A GANTRY IS 45 DEGREES)

NUCLEAR MAGNETIC RESONANCE DIAGNOSING DEVICE AND DIAGNOSING SYSTEM

This application claims priority and the priority date under 35 U.S.C. § 119 of Japanese Patent Application 2001-196528, filed on Jun. 28, 2001.

BACKGROUND OF THE INVENTION

1. Field of the Invention

The present invention relates to a nuclear magnetic resonance diagnosting apparatus (MRI apparatus).

2. Prior Art

The MRI apparatus is used for diagnosing an examined person by continuously obtaining tomograms at a part of inspection in the inspected person using the nuclear magnetic resonance (NMR) phenomenon. In order to produce the NMR phenomenon at the part of inspection of the examined person, the MRI apparatus is required to generate a magnetic field and to put the part of inspection of the examined person inside the magnetic field.

In a conventional MRI apparatus, a tunnel-shaped hole is generally formed inside a high-intensity magnetic field to lay an examined person inside the hole. Although the apparatus of this kind can easily generate the high-intensity magnetic field, there is the problem that inserting the examined person into the narrow hole makes it difficult to perform the inspection. Therefore, the conventional MRI apparatus has been designed so as to generate the NMR phenomenon by supporting a magnet with columns without using the tunnel-shaped hole, that is, space. Although most of the conventional MRI apparatuses employ methods of supporting the magnet with two columns, as described in Japanese Patent Application Laid-Open No. 8-140958, a method of supporting the magnet with a single column is also proposed.

DISCLOSURE OF THE INVENTION

In a case where a doctor and others execute both of inspection and medical treatment at a time, particularly in a case of inspection of a head part, they execute the medical treatment by inserting instruments such as needles into the part of inspection while observing an image of the part. In such a case, wide open spaces are required in both right-hand side and left-hand side of the doctor because the doctor and others execute plural kinds of work and the instruments are arranged. There have been conventional apparatuses in which an examined person is laid so as to be perpendicular to a straight line passing through its wall. (column) and its center of measurement space. Therefore, in a case where medical treatment is performed to a part of measurement in an abdominal part of the examined person from an open face opposite to the wall (column) among three open side faces, the doctor can obtain open spaces in both of his right-hand side and his left-hand side by standing at the open space opposite to the wall face, but he can not obtain substantially wide open spaces by being blocked with a support mechanism of a bed for laying the examined person and the head part and the leg parts of the examined parson himself. In a case of performing medical treatment to the head part, an open space is limited to the space opposite to the wall face (column) because either the right-hand side or the left hand-side of the head part of the examined person faces the wall face (column), and the limited open space is the only accessible space of the doctor and others. Accordingly, the conventional apparatus has a problem of difficulty of use.

In addition, when the apparatus is installed in a narrow examination room, it is difficult to secure an open space necessary for medical treatment because a gap between the wall face of the examination room and the apparatus is small.

In taking the above problems into account, an object of the present invention is to improve accessibility of a doctor and others to an examined person by forming continuous and wide open-areas around an examining table and to provide an MRI apparatus which can form a wide open space particularly over 180 degrees or more.

Further, another object of the present invention is to further improve the operability and to provide an MRI apparatus which can be effectively installed in a narrow space.

The present invention is characterized by a nuclear magnetic resonance diagnosing apparatus for continuously taking tomograms of an examined person in a space formed between a pair of magnets which comprises a cylindrical table top support of gantry side; the pair of magnets vertically arranged, the table top support of gantry side being interposed between the pair of magnets; and a column for supporting at least the magnet arranged in an upper side between the pair of magnets, which further comprises a support system having a slide table sliding on the table top support of gantry side; a slide table support means for mounting the slide table, the slide support means being arranged in a periphery of the table top support of gantry side and in a radial direction along the periphery; and a slide drive unit for the slide table, wherein the upper magnet is covered with a top magnet cover, the under magnet being covered with an examining table body, the column being formed as the only one column body having the same plane in common with the slide table between the upper magnet and the examining table body, a width of the column body determined by tangent lines passing through a center of the table top support of gantry side being smaller than a width of the table top support of gantry side or the like.

Further, the present invention is characterized by that the slide table is arranged in a radial direction within a movable range α1 and is slid on the table top support of gantry side, the movable range starting from one side of a range which is formed by a line passing through the center of the table top support of gantry side and perpendicular to a rotation center line passing through the center of the table top support of gantry side and extended toward the column body and the rotation center line in the side of the column and ending in the other side, the movable range being larger than 200 degrees and smaller than 270 degrees in angle and being a range of angle limited by the column body.

The present invention is characterized by that a connecting part between the table top support of gantry side and the bridge construction is placed in quadrants in a side of the column away from a straight line which passes through a center of the table top support of gantry side and crosses at right angles with a straight line passing through the center of the table top support of gantry side and a center of the column, and the connecting part is a portion both ends of which are set back inward from straight lines perpendicular to the straight line crossing at right angles and extended toward the column from points where the straight line crossing at right angles of the table top support of gantry side and a rim of said table top support of gantry side intersect each other.

The table top support of gantry side is generally formed circular.

Further, the present invention provides nuclear magnetic resonance diagnosing apparatuses combining the above-mentioned constructions.

BRIEF DESCRIPTION OF DRAWINGS

FIG. 19 is a detailed side view showing a bed 3;

FIG. 20 is a plan view of FIG. 19;

FIG. 23 is a plan view of FIG. 22; and

FIG. 24(1), FIG. 24(2), FIG. 24(3) and FIG. 24(4) are views showing modified examples of the table top support of gantry side 11.

DESCRIPTION OF THE PREFERRED EMBODIMENTS

Embodiments of the present invention will be described below, referring to accompanied drawings.

Figure 1:
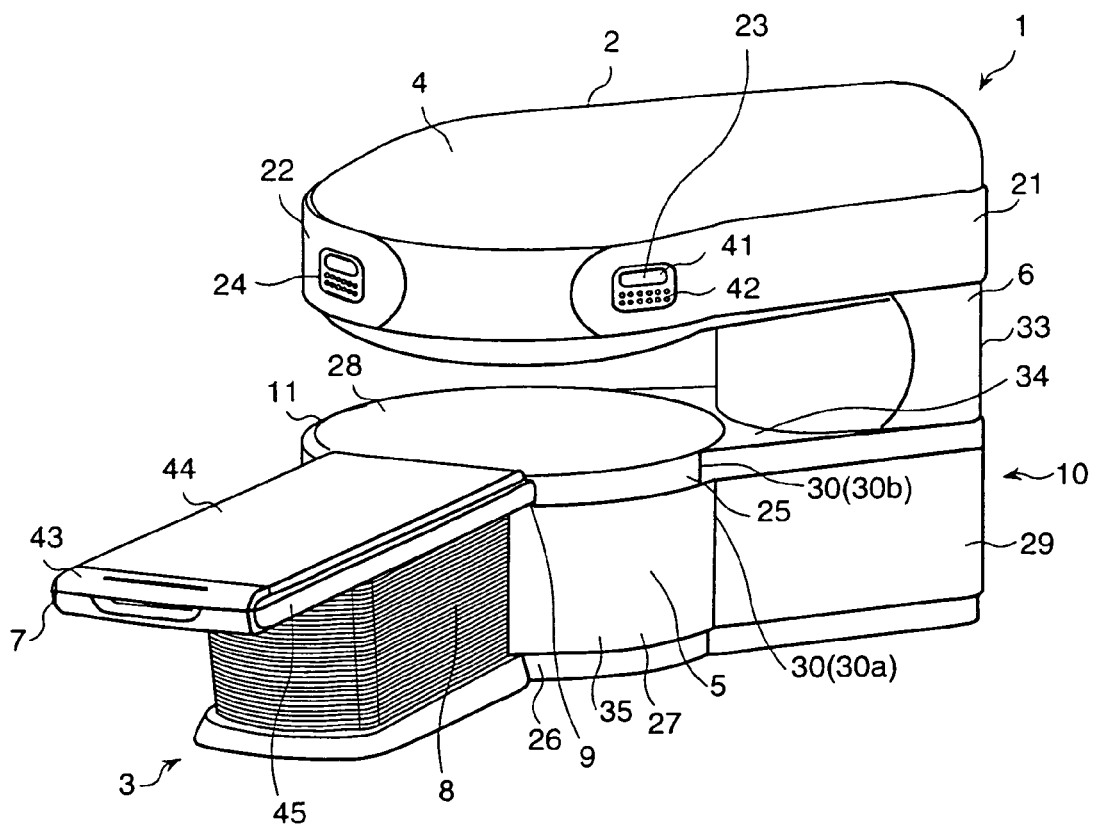
FIG. 1 is a sketch drawing showing the construction of an embodiment according to the present invention.
Figure 2:
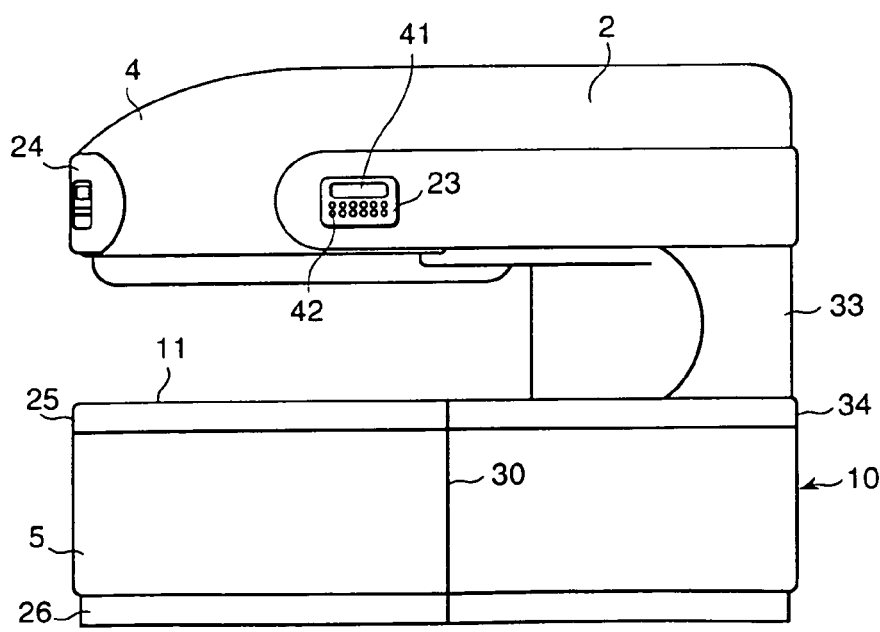
FIG. 2 is a side view of FIG. 1.

FIG. 1 to FIG. 5 show an embodiment of an MRI apparatus according to the present invention. Referring to FIG. 1 and FIG. 2, a gantry 2 of the MRI apparatus 1 is composed of an upper magnet cover 4; an under magnet cover 5; a bed 3 as a supporting system; a column 6; and a table top support of gantry side 11. The box-shaped upper magnet cover 4 has side covers 21 and 22 formed in the side face nearly vertically to enhance the appearance of the apparatus.

Control panels 23 and 24 are provided on the side covers 21 and 22, respectively, to make it possible to operate the whole MRI apparatus. More specifically, the MRI apparatus 1 is controlled by a computer, not shown, containing a memory unit storing various kinds of data, and instruction is input from the control panel 23 or 24. Each of the control panels 23 and 24 has a display 41 of a screen part and switches 42 of an input part, and operation of the apparatus can be performed while checking input values on the screen.

The table top support of gantry side 11 is nearly circular box-shaped, and includes a horizontal circular part 28 and a table top support circular contacting surface 25 of a circular contacting surface arranged the upper end portion and a box 27 having a circular space containing a tip of foot 26 arranged the lower end portion. The under magnet cover 5 is arranged between the table top support circular contacting surface 25 and the space containing a tip of foot 26, and is installed parallel to the table top support circular contacting surface 25. The top surface of the table top support of gantry side 11 is the horizontal circular part 28 on which a slide table 43 is mounted.

Figure 4:
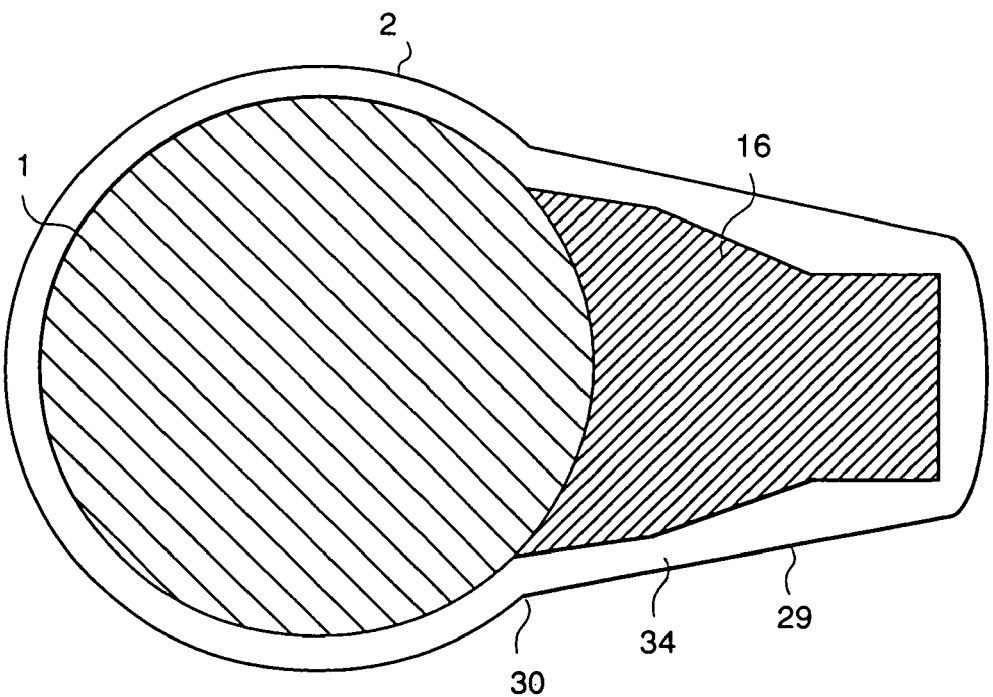
FIG. 4 is a cross-sectional plan view of FIG. 1.

The box 27 is formed as a box part integrated with a column cover 33 of the column 6. A box part 29 integrated with the column cover 33 is of a trapezoidal rectangular parallelepiped in cross section, as shown in FIG. 4. Accordingly, the box 27 is composed of the circular box-shaped part and the rectangular parallelepiped part, and the connecting face is defined as a connecting part 30. Therein, the connecting part 30 may have a more distant structure. The integrated box 27 is a box for the table top support of gantry side 11, and the table top support of gantry side 11 is formed on the integrated box 27. Therefore, the box 27 under the table-top support of gantry side 11 includes the under magnet cover 5, and covers the under magnet 18.

In a case where the box 27 has the box main part 35 and the table top support of gantry side 11 and the table top support circular contacting surface 25, as shown in FIG. 1, the connecting parts are formed in both of the box main part 35 and the table top support of gantry side 11. (The connecting parts are denoted by 30a, 30b)

Figure 3:
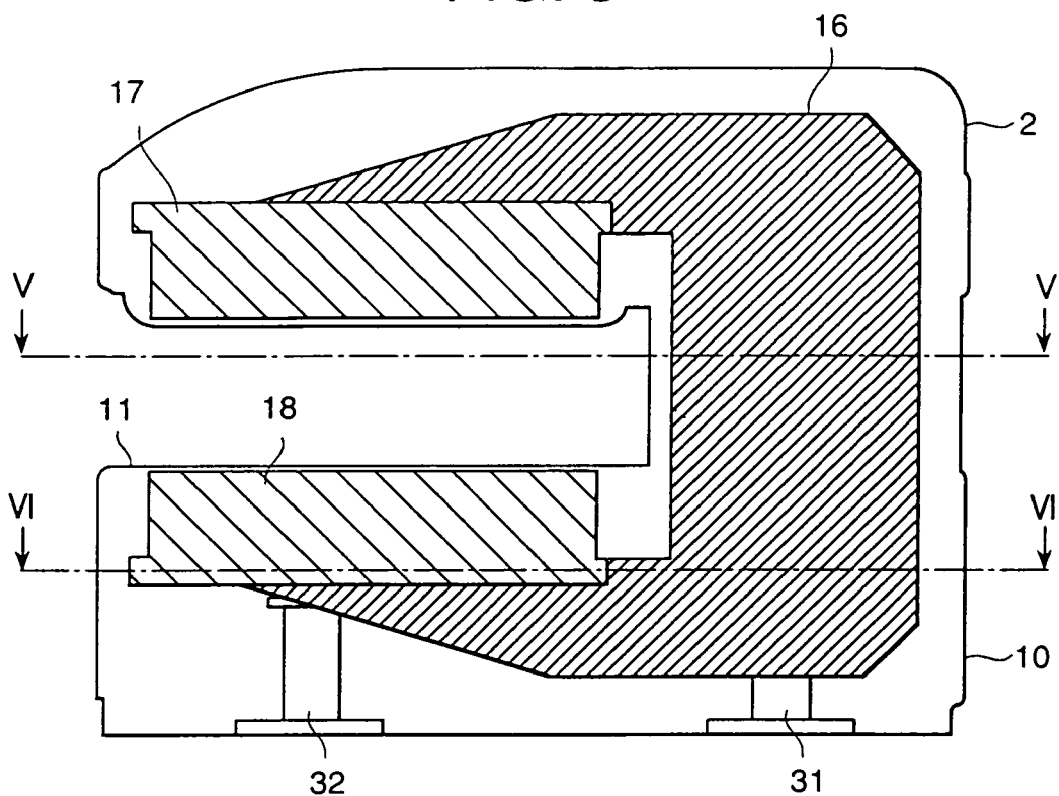
FIG. 3 is a cross-sectional vertical view of FIG. 1.

FIG. 4 shows a cross section VI—VI of FIG. 3.

As shown in FIG. 3 and FIG. 4, the upper magnet 17 and the under magnet 18 are spaced horizontally and oppositely to each other inside the upper magnet cover 4 and the under magnet cover 5, respectively. The upper magnet 17 and the under magnet 18 are each disk-shaped, and are supported by an iron column main body 16 having a function of securing a flux path. These units are supported by other columns 31, 32.

Therefore, the column 6 in the present embodiment is composed of the column main body 16 for supporting the upper magnet 17 and the under magnet 18 and a column cover 33 covering the column main body and integrated with the upper magnet cover 4, and is a unit having surfaces exposed to the external, and forms part of the gantry 2.

A bridge construction 34 is arranged on the upper face of the box part 29 between the column 6 and an examining table body 10. The bridge construction 34 is composed of a horizontal flat plane connecting the periphery of the column 6 and the table top support of gantry side 11, the box 27 and the table top support circular contacting surface 25 which forms a part of the box part 29.

The column 6 in the present embodiment is unified to the only one structural body for connecting the examining table body 10 to the upper magnet cover 4, and accordingly, the column 6 can reduce the installing area (angle) for the column 6 to be arranged around the table top support of gantry side 11. Employing of the table top support of gantry side 11 having a small installing area increases an allowable installing area for the bed 3, and therefore, can provide a continuous and wide open space.

A heat insulating material 19 is disposed in a gap portion inside the gantry 2 or inside the column 6. Referring to FIG. 1, the bed 3 (support system) is set at any position around the table top support circular contacting surface 25 of the table top support of gantry side 11.

The bed 3 is composed of a bed table top 7, a part of a table top 45 (table top hold) and a table top support of table 8 for supporting the table top 45 (the both compose a slide table support means), and a slide table 43 is slidably mounted on the table top 45, and a mat 44 is mounted on the slide table 43. Further, a holding plate 45, on which the slide table 43 is slid, is provided. The slide table 43 can be slid onto the table top support of gantry side 11 by a drive mechanism, not shown. In this case, the top end portion of the table top 45 of the table top hold serves as a connecting part 9 to the table top support circular contacting surface 25. The table top 45 is usually used by bringing the connecting part 9 in contact with, that is, by connecting the connecting part 9 to the table top support circular contacting surface 25, but the table top 45 may be used by keeping a somewhat small distance between them. The box 27 may be set back inward from the table top support circular contacting surface 25. An accordion cover is used in the periphery of the table top support of table 8, and an up/down drive unit, not shown, composed of link mechanisms is installed inside the table top support of table 8.

Figure 5:
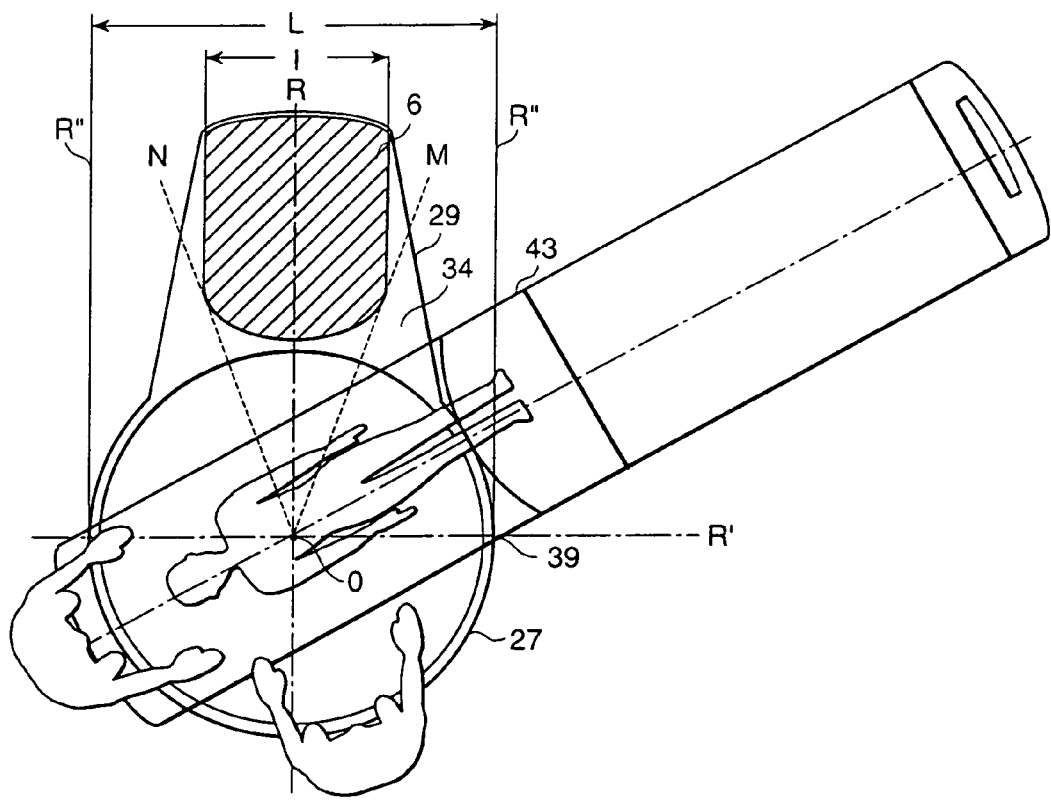
FIG. 5 is a view showing the relationship between a column 6 and a table top support of gantry side 11 (or a box 27)

FIG. 5 shows a cross section V—V of FIG. 3.

FIG. 5 also shows the relationship between a width l of the column 6 and a width L, such as diameter or the like, of the table top support of gantry side 11. Letting a width determined by contacting lines (hereinafter, referred to as tangent lines) M, N drawn from a center O so as to come in contact with peripheral corner portions in the front side of the column 6 be l (in a case of a rectangle, l), and a diameter of the examining table body be L, one of outstanding features of the present embodiment is that the apparatus has the only one support body and l<L.

Figure 6:
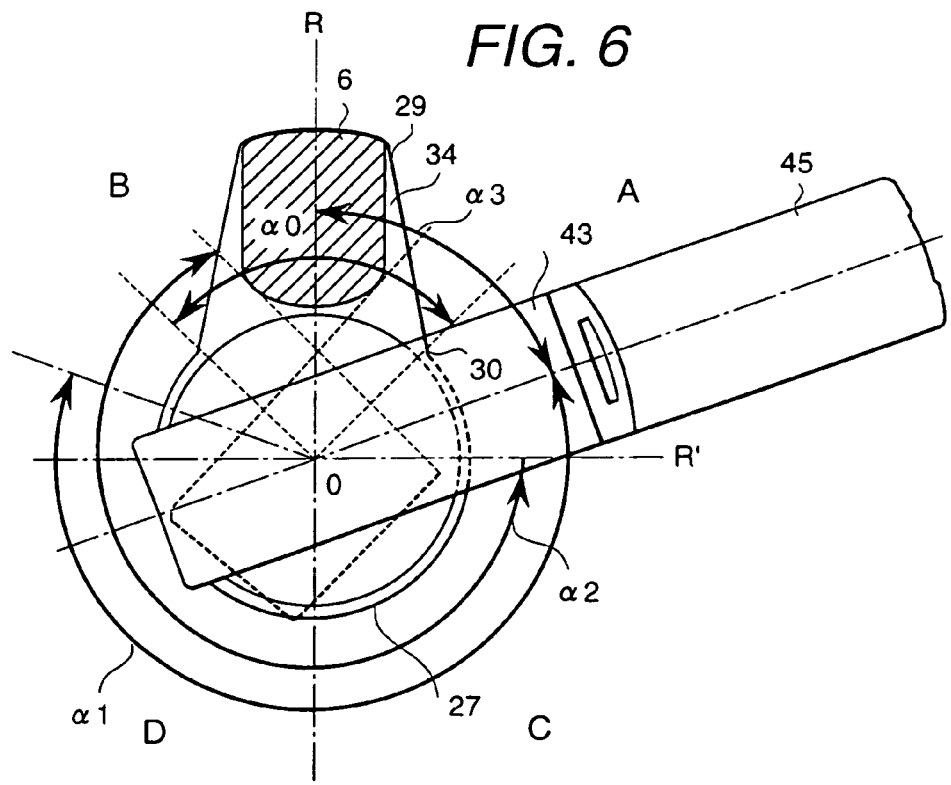
FIG. 6 is a plan view showing a main part of FIG. 1.

FIG. 6 is a view explaining the relationship between the slide table 43 sliding onto the table top support of gantry side 11 and the column 6, that is, explaining an arrangement limit of the slide table 43.

The above-mentioned connecting part 30 has a function of preventing the table top support of table 8 for supporting the slide table 43 from being set toward the column 6 of the table top support of table 8 for supporting the slide table exceeding the connecting part 30, and has a function of a setting control part or a setting blocking part. This is the construction produced by that a line connecting between the column 6 and the table top support of gantry side 11 is set back toward the inside from a line extending from an intersection of an orthogonal line with respect to the center of the table top support of gantry side and the rim of an examining table toward the column in a direction perpendicular to the orthogonal line, as shown in FIG. 5.

The slide table 43 can be moved up to a setting limit exceeding the position shown in the figure until the holding table top 45 or the table top support of table 8 comes in contact with the column 6 unless the holding table top 45 or the table top support of table 8 is blocked or worn by the box part 29. Accordingly, in order to obtain a wider open space, it is important to make the lateral width of the column narrower. Therefore, the condition l<L is employed, as described above.

In other words, as shown in FIG. 5, a line (the connecting part 30) connecting between the bridge construction 34, which is placed between the column and the table top support of gantry side, and the table top support of gantry side 11 is set back from a line R" extending toward the column in a direction perpendicular to an orthogonal line R', which passes through the center of the table top support of gantry side and is orthogonal to a centerline R connecting between the center of the table top support of gantry side and the center of the column, from a portion 39 where the orthogonal line R' and the rim of the examining table intersect each other.

The setting position of the slide table 43 capable of obtaining such a wide open space can be determined by setting the following condition to the surrounding of the table top support of gantry side 11.

Referring to FIG. 6, letting a centerline passing through the center 0 of the table top support of gantry side 11 and drawn toward the center of the column 6 be a center line R, and letting a line passing through the center of the table top support of gantry side 11 and orthogonal to the centerline R be an orthogonal line R', the first quadrant A and the second quadrant B are formed in the side of the column by the centerline R and the orthogonal line R', and the third quadrant and the forth quadrant C are formed in the opposite side of the column.

The traveling range of the setting position of the slide table 43 is determined by the range starting from the first quadrant A and ending in the second quadrant B through the forth quadrant C and the third quadrant D, as shown by a solid line.

The example of FIG. 6 shows the condition that the table top support of table 8 for supporting the slide table 43 can not move toward the column side by coming in contact with the connecting part 30, that is, by being limited by the bridge construction 34 of the box part 29, and an angle α3 in this case is set to 70 degrees. Therefore, in this example, the slide table 43 can travel up to the second quadrant B through the third quadrant D and the fourth quadrant C symmetrically with respect to the centerline R.

The traveling range in this case becomes 220 degrees which consists of 180 degrees of traveling range in the third quadrant D and the fourth quadrant C and (90−70)×2=40 degrees of traveling range in the first quadrant A and the second quadrant B. Therein, an angle α0 is 90 degrees.

In the above-mentioned case where an angle α3 of 45 degrees can be realized by the construction of the table top support of table 8 of the slide table and the construction of the bridge construction 34 for connecting the connecting part 30 between the column 6 and the table top support of gantry side 11, the traveling range becomes 270 degrees.

In other words, in a case where the table top support of table 8 can be moved until the side face of the slide table 43 comes in contact with the peripheral corner portions in the front side of and in right hand and left hand sides of the column 6 when seeing from the upside of the drawing plane, as shown in FIG. 6, since the center 0 of the table top support of gantry side 11 and the centerline of the slide table are overlapped each other, as shown by dot lines, a wider open space can be obtained by further setting the allowable angle α3 between the centerline of the slide table 43 and the centerline R to about 45 degrees. It has been found from a functional evaluation that a preferable traveling range from the viewpoint of observing a examined person is 220 degrees to 240 degrees. This traveling range may be further expanded to set 200 degrees to 270 degrees.

Although the above-described example is the case that the maximum limited range of the slide table 43 is limited by the column 6, it is only natural that there is a case where the maximum limited range is limited by coming of the holding table top 45 (or the table top support of table 8) for mounting the slide table 43 in contact with the pox portion 29. In such a case, the maximum limited range is selected within a range of 200 degrees to 260 degrees, and it is possible to set the angle within a range of 200 degrees to 260 degrees.

Further, in FIG. 6, the angle α1 indicates a traveling range in the circumferential direction of the bed, that is, a setting range in the circumferential direction of the bed, the angle α2 indicates an open space angle when a doctor and others stand in the left hand side of the bed 3, and the angle α3 indicates an angle between the centerline connecting the center of the column and the center of the table top support of gantry side and the centerline of the bed.

When the angle α3 between the centerline connecting the center of the column 6 and the center of the table top support of gantry side and the centerline of the bed is set to 70 degrees, the angle α1 of the traveling range in the circumferential direction of the bed 3, that is, the range of connectable angle of the bed 3 to the table top support of gantry side 11 is 220 degrees, as described above.

On the other hand, the open space α2 is an angle of the sum of the angle 180 degrees of the third quadrant D and the fourth quadrant C and the angle of the second quadrant B up to the column. In this case, by setting an angle between the centerline R and the tangent line drawn from the center of the table top support of gantry side to the peripheral corner portion in the front side of the column 6 so as to come in contact with the peripheral corner portion to about 30 degrees, the open space α2 becomes 180+(90−30)=240 degrees, and accordingly, a sufficient wide open space can be obtained.

The above-described example is the case that the table top support of table 8 for supporting the slide table 43 can not travel any more toward the column side because of coming in contact with the connecting part 30.

Considering a case where the limitation due to the connecting part 30 is released by detaching the table top support of table 8 from the connecting part 30, the setting position of the slide table 43 in this case is limited by the column 6 because the limitation is determined until the slide table comes in contact with the column 6.

That is, the slide table 43 is arranged opposite to the table top support of gantry side and within a possible setting range α1 starting from one quadrant in the side of the column and ending in the other quadrant in the side of the column, and the possible setting range is larger than 200 degrees in angle and is an angle limited by the column 6.

It is preferable that the slide table 43 is arranged opposite to the table top support of gantry side and within a possible setting range α1 starting from one quadrant in the side of the column and ending in the other quadrant in the side of the column, and the possible setting range is larger than 240 degrees in angle and is an angle limited by the column 6.

Figure 7:
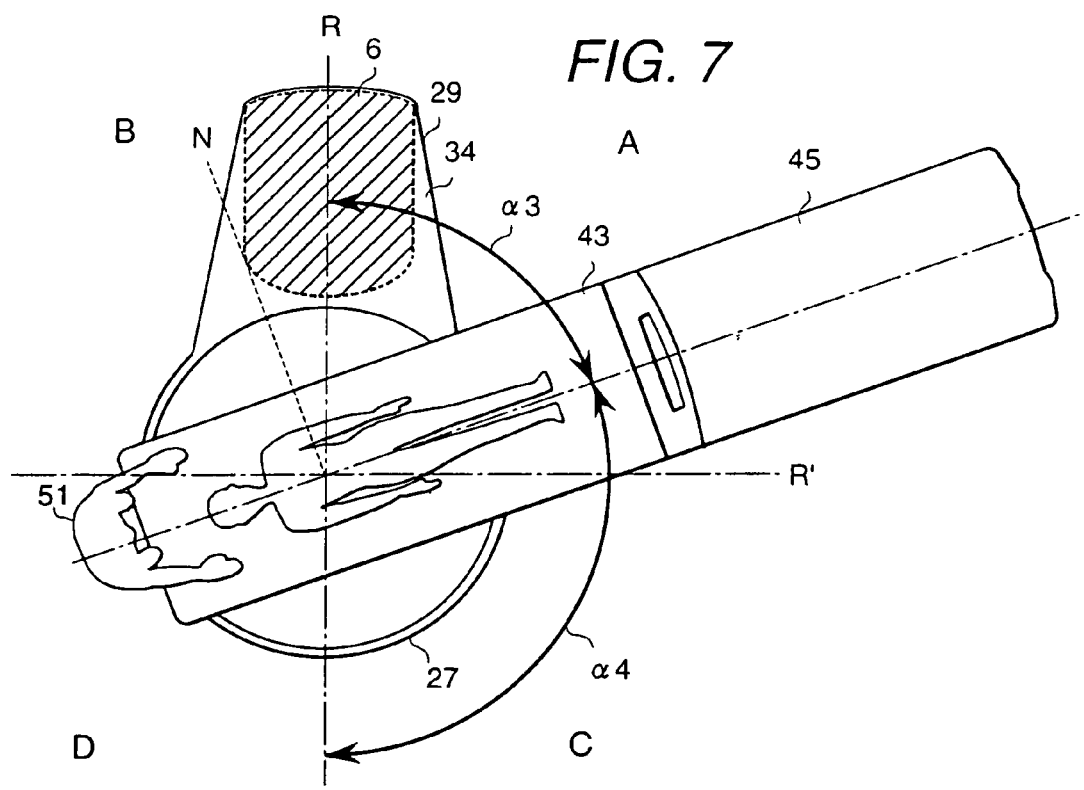
FIG. 7 is a view showing the relationship when a technical expert is standing.

FIG. 7 shows a case where a medical expert or a doctor 51 is standing near the table top support of gantry side 11 when the angle α3 between the centerline R of the column 6 and the centerline of the bed 3 (the slide table 43) is set to 70 degrees.

The angle α4 is a traveling range starting from the first quadrant A which is one of ranges in the column side of the straight line R' orthogonal to the centerline R and passing through the center of the table top support of gantry side 11, and indicates an angle range up to the centerline R in the fourth quadrant C. In this case, the traveling range α4 becomes 180−70=110 degrees.

The angle 0.4 is a traveling range starting from the first quadrant A which is one of ranges in the column side of the straight line R' orthogonal to the centerline R and passing through the center of the table top support of gantry side 11, and indicates an angle range up to the centerline R in the fourth quadrant C. In this case, the traveling range 0.4 becomes 180−70=110 degrees.

Letting a movable range of the medical expert or the doctor to the bed 3 in the second quadrant B, that is, a traveling range up to the column 6 be 45 degrees, the traveling range in the second and the third quadrants becomes 180−45=135 degrees.

Thus, the traveling range described above becomes α2=110+135=245 degrees, and accordingly, an angle range above 240 degrees can be secured.

Here, an angle of open space will be defined. On the premise that the slide table 43 has generally a nearly equal width in the condition of FIG. 7, the angle of open space is defined as an angle up to the column 6 by measuring from the orthogonal line R' in the fourth quadrant passing through the center 0 of the table top support of gantry side 11 and orthogonal to the centerline R when the setting angle α3 is set to 70 degrees.

Therefore, providing that in the example of FIG. 7 the angle between the centerline R and a tangent line N drawn from the center 0 toward the peripheral corner portion in the front side of the column 6 is 30 degrees, the angle of open space is 360−(90+30)=240 degrees by subtracting the angle of the first quadrant and the angle between the tangent line N drawn from the center 0 and the centerline R. That is, the wide open space angle of 240 degrees can be obtained to the traveling angle of 245 degrees.

One of the features of the present embodiment is that the wide open space angle of 240 degrees can be obtained, an open space angle equal or more to the traveling range of 200 degrees is preferably secured, and the traveling range α1 and the open space α2 overlap in most parts of these angles each other. Thereby, the movable area for the medical expert or the doctor can be expanded, and accordingly, a patient observing area to the examined person can be expanded.

Figure 8:
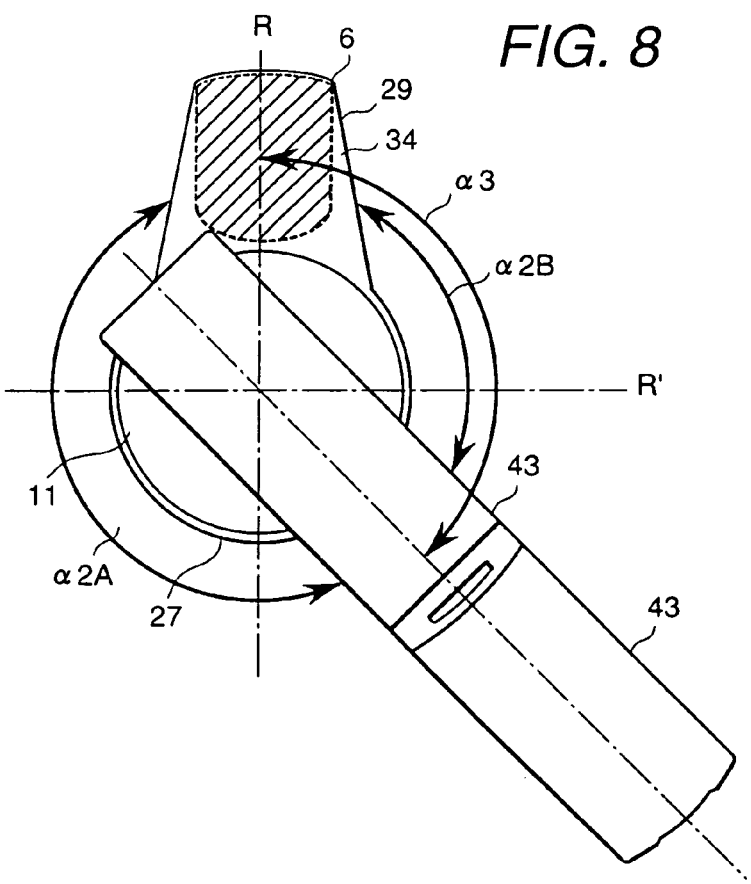
FIG. 8 is a view showing an operating example corresponding to FIG. 6.
Figure 9:
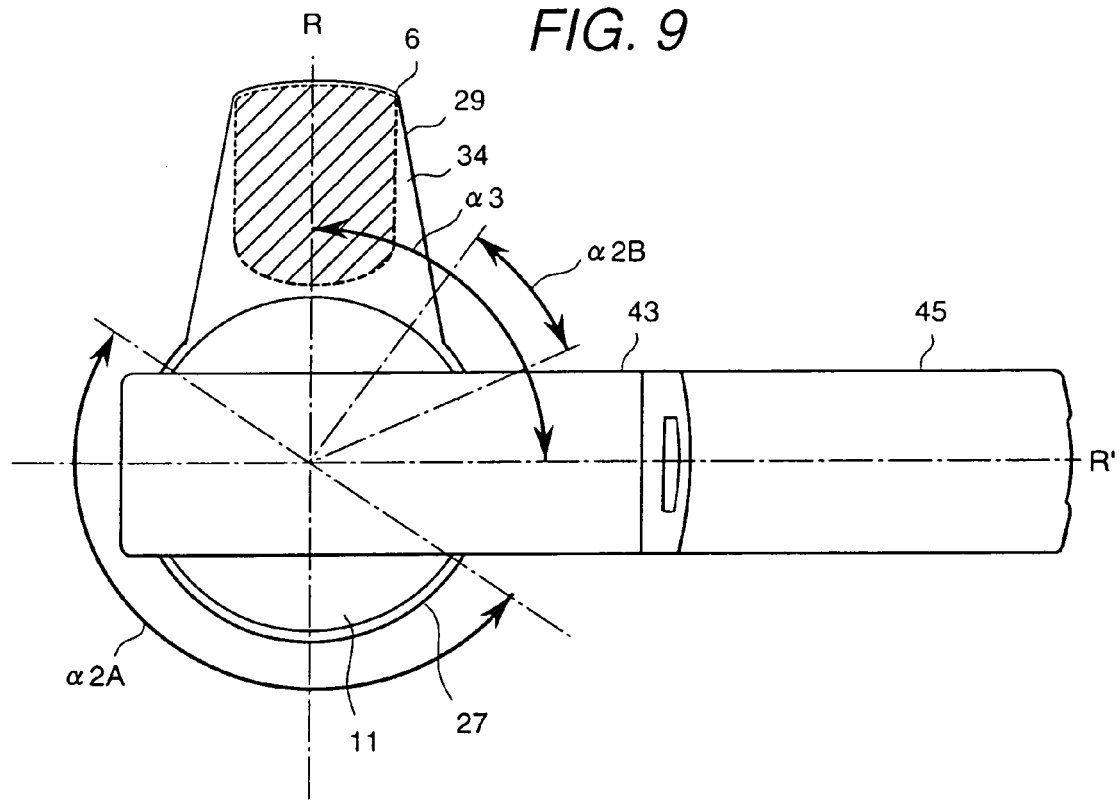
FIG. 9 is a view showing an operating example corresponding to FIG. 6.

FIG. 8 and FIG. 9 shows an example in a case where the setting position of the bed 3 is set by being rotated in the radial direction to bring the bed downward in the drawing compared to the state of FIG. 7.

In the case of FIG. 8, the setting angle α3 of the bed 3 is set to 115 degrees. In this case, although the open space angle α2A of the area in the left hand direction of the bed is decreased, but the area of α2B is increased by the amount of the rotation in the radial direction to compensate the decreased amount described above.

That is, the open space area as the total sum is essentially not changed because the open space angle α2B in the right hand side is increased though the open space angle α2A in the left hand side is decreased.

In the case of FIG. 9, the setting angle α3 is set to 90 degrees. In this case, although the open space angle α2A of the area in the left hand direction of the bed is decreased, but the area of α2B is increased by the amount of the rotation in the radial direction to compensate the decreased amount described above.

That is, the open space area as the total sum is essentially not changed because the open space angle α2B in the right hand side is increased though the open space angle α2A in the left hand side is decreased.

Figure 10:
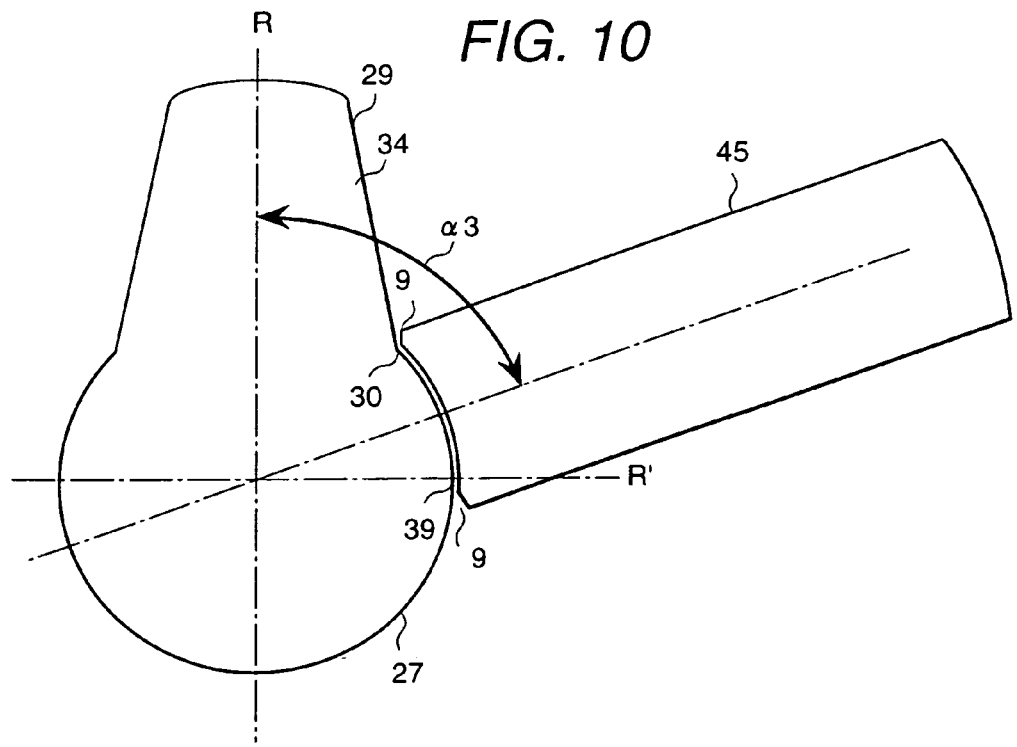
FIG. 10 is a view showing a modified example.

The example of FIG. 10 shows an example in which the both side ends of the table top 45 are cut out. By employing such a construction, the table top 45 can be brought closer to the column when the table top 45 is brought in contact with the connecting part 30.

That is, when the both side ends are not cut out, the table top 45 is kept at a distance from the column by the amount not having the cutout because the end portion of the table top is in contact with the connecting part 30.

Figure 11:
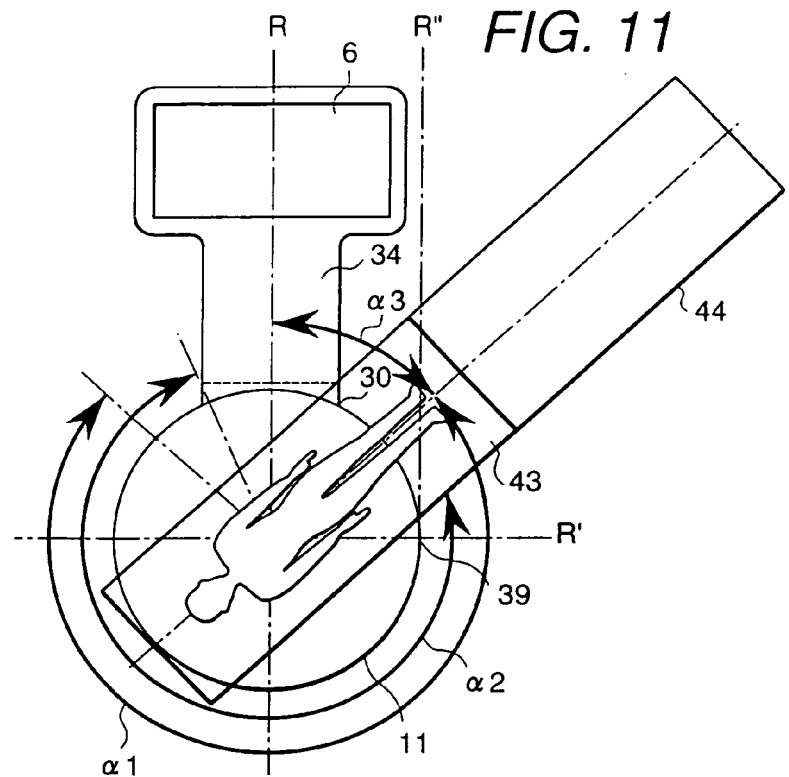
FIG. 11 is a sketch drawing showing the construction of another embodiment.

The example of FIG. 11 shows an example in which the column is arranged more distantly from the table top support of gantry side 11 than that in the example of FIG. 1, and the bridge construction 34 is arranged between the column and the table top support of gantry side, though this example is somewhat disadvantageous from the viewpoint of the installation area.

In this example, a line (the connecting part 30) connecting between the bridge construction 34, which is placed between the column and the table top support of gantry side, and the table top support of gantry side 11 is set back toward the centerline R from the line R" extending toward the column in the direction perpendicular to the orthogonal line R', which passes through the center of the table top support of gantry side and is orthogonal to the centerline R connecting between the center of the table top support of gantry side and the center of the column, from the portion 39 where the orthogonal line R' and the rim of the examining table intersect each other. Both the connecting part 30 and the bridge construction 34 in this example are set back toward the centerline R from the line R" extending toward the column in a direction perpendicular to the orthogonal line R'.

By such a construction, a wide traveling angle α1 and a wide open space angle α2 can be also obtained, and the movable area for the medical expert or the doctor can be expanded, and accordingly, a patient observing area to the examined person can be expanded.

Figure 12:
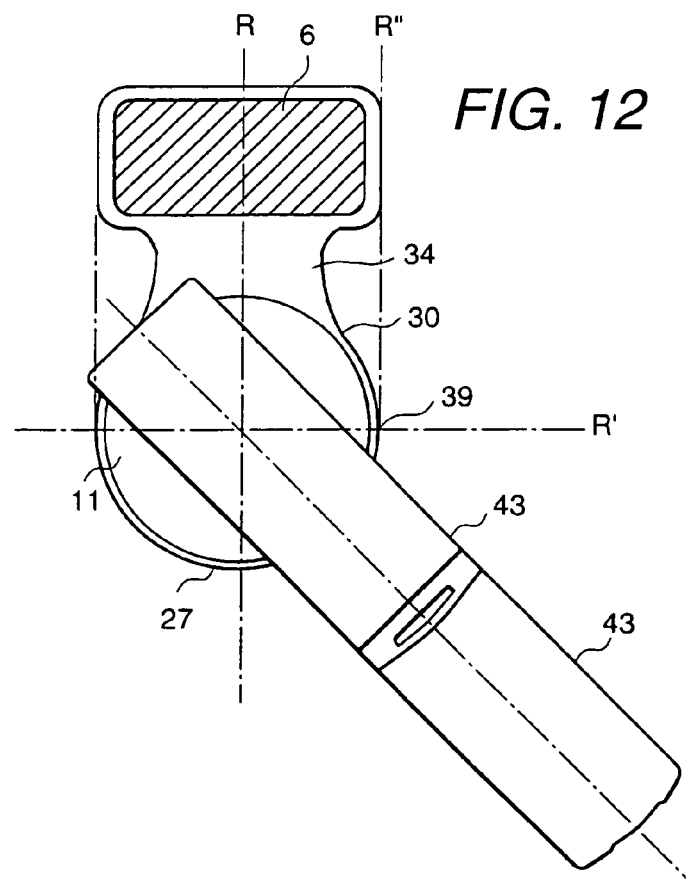
FIG. 12 is a view showing a modified example of FIG. 11.

FIG. 12 shows a modified example of FIG. 11 in which the set-back state of the bridge construction 34 is formed by combining straight lines and curved lines.

In this example, a line (the connecting part 30) connecting between the bridge construction 34, which is placed between the column and the table top support of gantry side, and the table top support of gantry side 11 is set back toward the centerline R from the line R" extending toward the column in the direction perpendicular to the orthogonal line R', which passes through the center of the table top support of gantry side and is orthogonal to the centerline R connecting between the center of the table top support of gantry side and the center of the column, from the portion 39 where the orthogonal line R' and the rim of the examining table intersect each other.

Both the connecting part 30 and the bridge construction 34 in this example are also set back toward the centerline R from the line R" extending toward the column in a direction perpendicular to the orthogonal line R'.

The feature in this case is that each of the traveling range angle α1 and the open space angle α2 can be set to 180 degrees or more, for example, set to 220 degrees by incorporating ideas into the shape of the bridge construction 34.

By such a construction, a wide traveling angle α1 and a wide open space angle α2 can be also obtained, and the movable area for the medical expert or the doctor can be expanded, and accordingly, a patient observing area to the examined person can be expanded.

Figure 13:
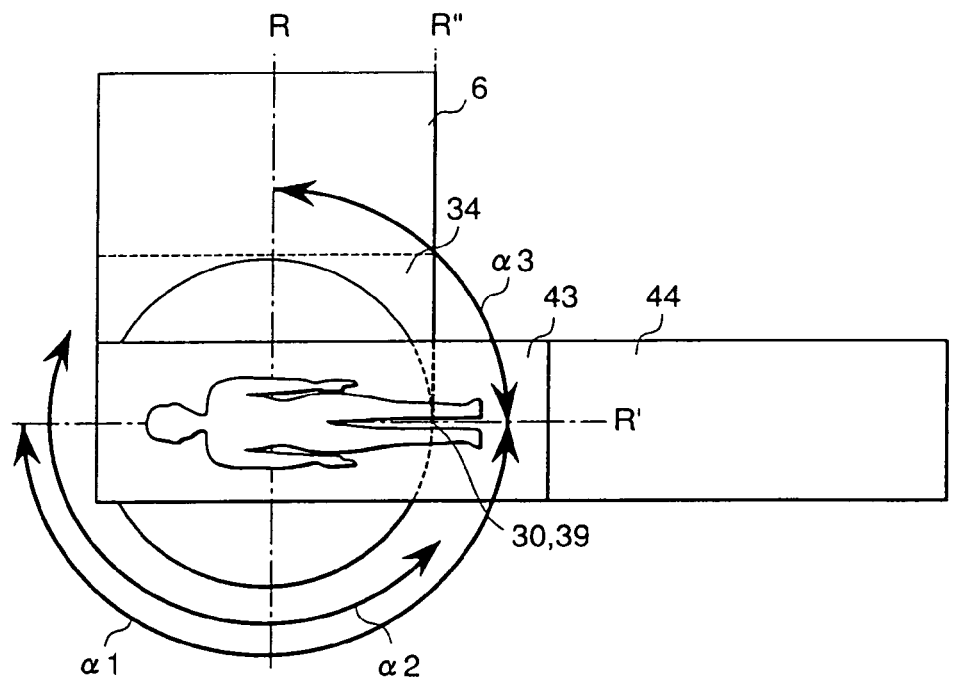
FIG. 13 is a view showing a comparative example.

The example of FIG. 13 shows a comparative example in which the width of the column 6 is equal to or larger than the width of the table top support of gantry side 11.

In this example, the width of the connecting part 30 and the diameter of the rim of the examining table 39 agree with each other, and the line R" is also on the same line as the side end of the bridge construction, as shown in the figure, and accordingly, each of the traveling range angle α1 and the open space angle α2 is limited to nearly 180 degrees.

Figure 14:
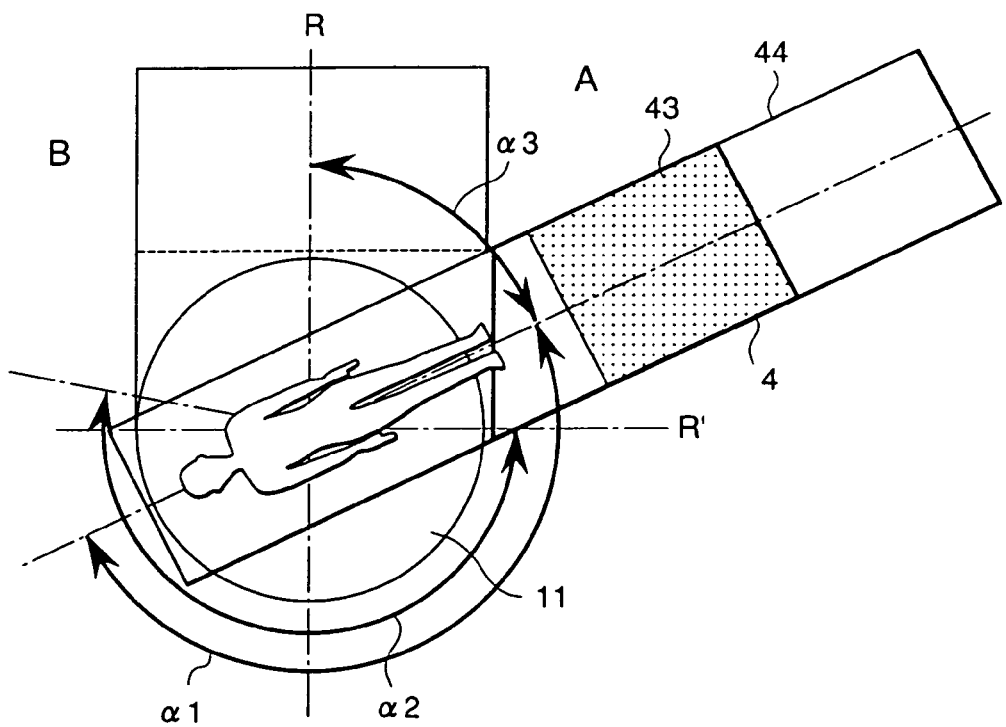
FIG. 14 is a view showing a modified example of the comparative example.

The example of FIG. 14 is a modified example of the construction shown in FIG. 13 of which the intention is to expand the traveling range angle α1 and the open space angle α2 by modifying the shape of the bed 3.

That is, the shape of the table top support of table of the bed 3 or the table top 45 is formed trapezoidal by beveling the portion in contact with the bridge construction 34 depending on the shape of the column 6, as shown in the figure.

In this case, although it is certain that the open space angle α2 is slightly expanded, the traveling angle α1 remains in 180 degrees, and the change in the shape for expanding the open space angle is necessary, and there is possibility of lacking in accuracy at setting the table top support of gantry side 11 of the bed 3.

In addition, there are problems that the table top support of table 8 or the table top 45 can not be set in the circular table top support of gantry side due to difference in the shape, and that the operability is not easy.

The setting position of the control panel 23 will be described below.

Referring to FIG. 1, as described above, the gantry 2 covering the upper magnet 2 has the upper magnet cover 4, and the upper magnet cover has the side cover 21 the surface of which is in the vertical direction, and the cover is composed of the upper magnet cover 4 and the side cover 21. The side cover 21 has the control panel(s) 23 of the MRI apparatus 1 arranged within one of ranges formed by the centerline R connecting through the center 0 of the table top support of gantry side 11 and the center of the column and the orthogonal line R' passing through the center 0 of the table top support of gantry side 11 and crossing with the centerline R at right angles or within both of the ranges of the fourth quadrant C and the third quadrant D.

In the example of FIG. 1, a first control panel 23 is arranged in the area of the fourth quadrant C, and a second control panel 24 is arranged on the line R, but these control panels have a similar function or different functions.

As described above, there is an advantage that the operation becomes easier by arranging the control panel on the side cover 21 in the fourth quadrant C or the third quadrant D as the traveling range angle α1 is increased.

FIG. 15 and FIG. 16, and FIG. 17 and FIG. 18 show other embodiments of arrangement of the control panels.

Figure 15:
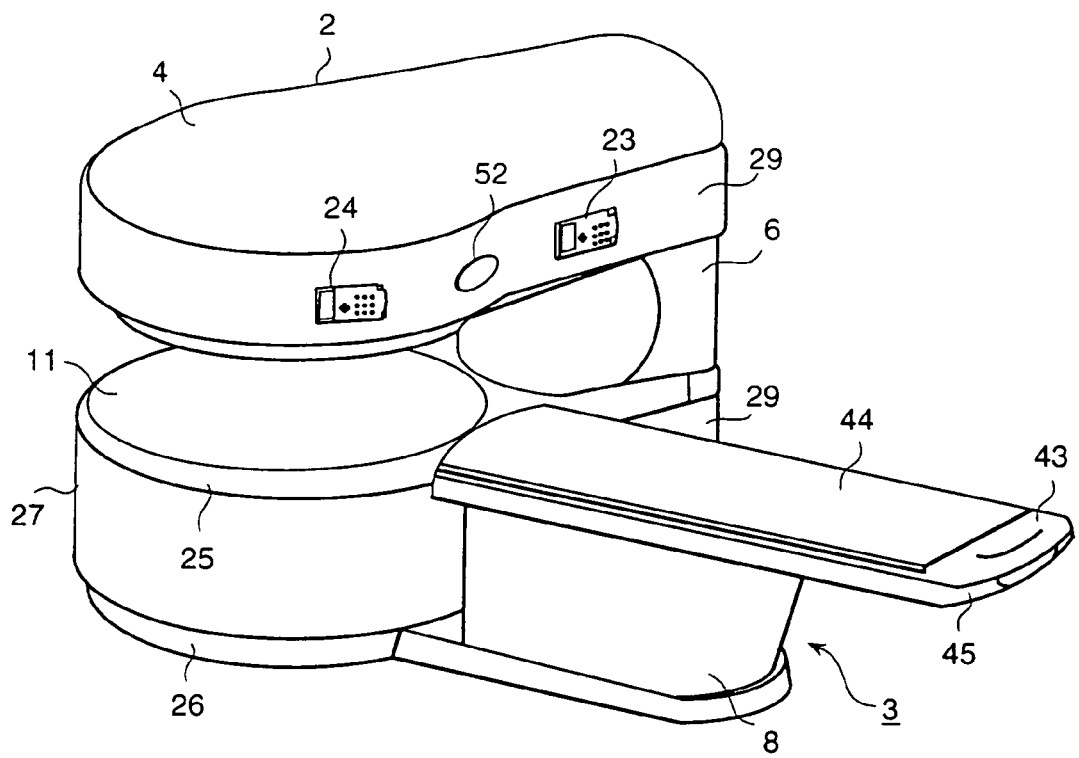
FIG. 15 is a view showing a modified example of control panel arrangement.
Figure 16:
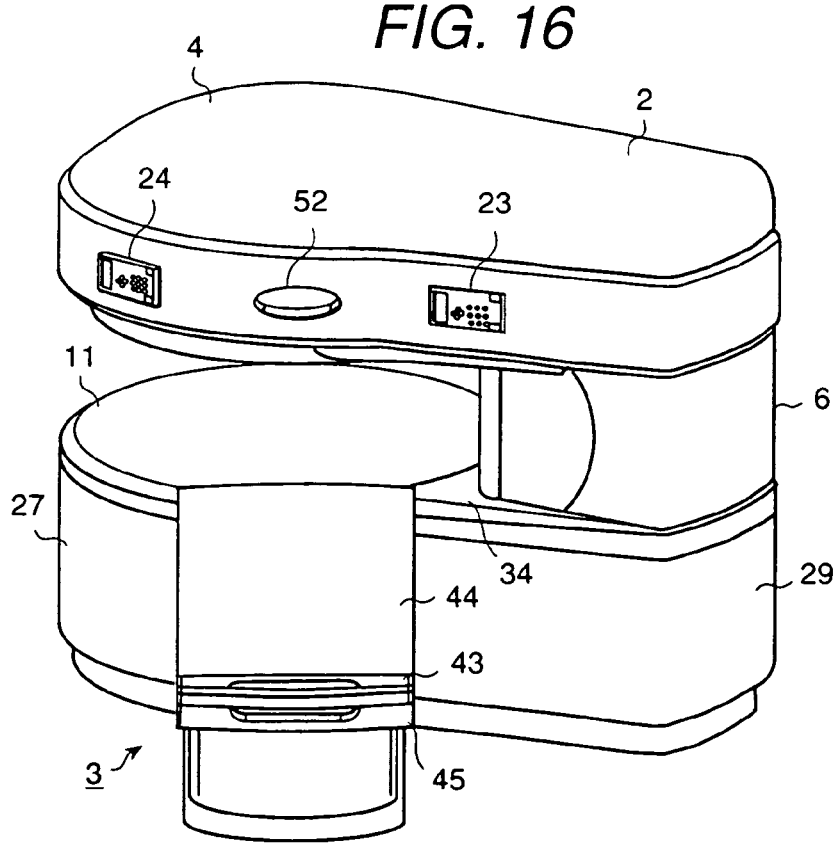
FIG. 16 is a side view of FIG. 15.
Figure 17:
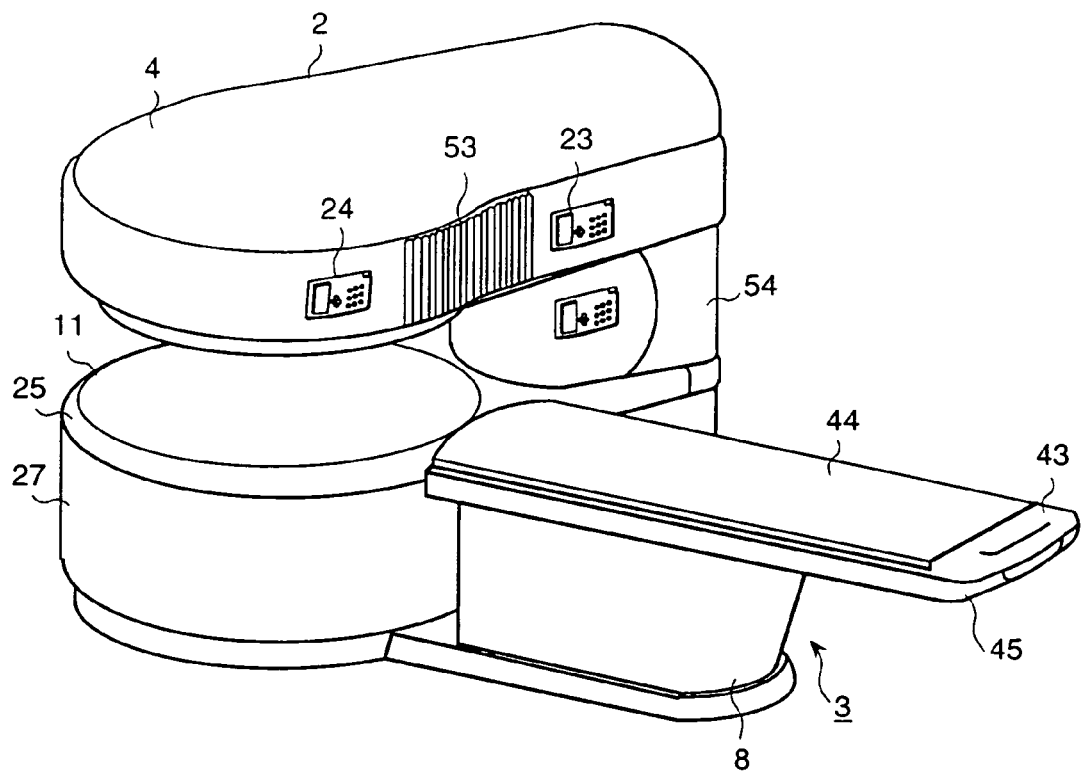
FIG. 17 is a view showing another modified example of control panel arrangement.
Figure 18:
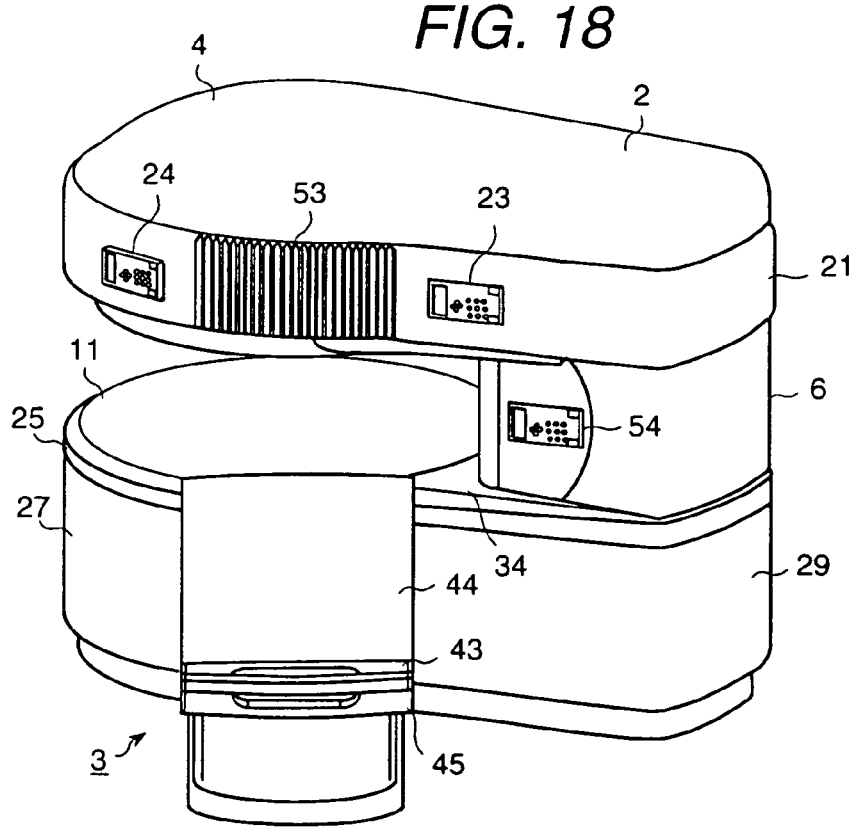
FIG. 18 is a side view of FIG. 17.

In the example of FIG. 15 and FIG. 16, the control panels 23 and 24 are arranged at an area in the first quadrant A and at an area in the fourth quadrant C, respectively.

Further, a badge 52 is arranged in a midrange between these control panels. The badge may be a nameplate marking of a manufacture. The badge indicates the front when a patient looks at the apparatus.

The example of FIG. 15 and FIG. 16 is an example which has a corrugated pattern 53 as the front marking, and the arrangement of the control panels 23 and 24 is the same as that in the example of FIG. 15 and FIG. 16. Further, in this example, a third control panel 54 is arranged on the column 6 to improve the operability.

FIG. 19 and FIG. 20 are a detailed view of the bed 3. FIG. 20 shows the details of the table top 45, and the both side end of the table top 45 are cut out so that the table top 45 can be closely moved toward the column when the table top 45 is brought in contact with the connecting part 30, as described in FIG. 10.

Further, the shape of the contact part 9 of the table top is conformed to the shape of the circular contact face 25 of the table top support of gantry side. Thereby, setting work of the bed 3 around the table top support of gantry side 11 becomes easy, and there is no gap between the table top support of gantry side and the bed.

Figure 21:
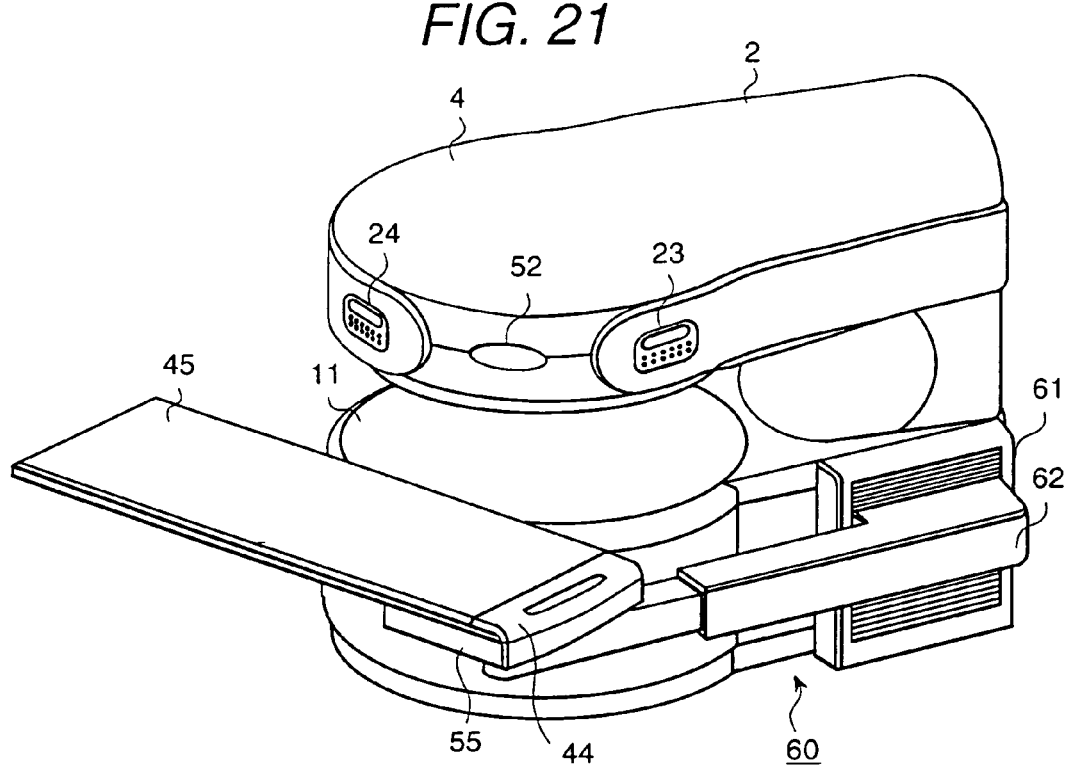
FIG. 21 is a modified example of a support system.

FIG. 21 shows an embodiment which shows another example of a support unit, and a support mechanism 60 is arranged instead of the bed 3. This embodiment is the same as the example shown in FIG. 1 except for the support mechanism 60, and explanations of the traveling range angle α1 and the open space range angle α2 are also the same as those of FIG. 1.

Although it is similar to the aforementioned explanation that the support mechanism 60 comprises the table top 45, the slide table 43 and the mat 44, the shape of the table top 45 is a short-length shape compared to the aforementioned table top.

The support mechanism 60 is integrated into the tabletop support of gantry side 11 at the portion of the box part 29, and the support mechanism 60 comprises an up/down drive unit 61, and up/down motion of the up/down drive unit 61 is transmitted to the table top 45 by an arm 62 extending in the horizontal direction to move the table top 45, that is, the slide table 43 in the horizontal direction.

The up/down drive unit 61 also has a rotation drive mechanism, not shown, controlled by a computer to rotate the table top 45 by a rink mechanism arranged inside the arm 62 or by electronic control of a motor.

By installing of the support mechanism 60, the setting position and sliding to the table top support of gantry side 11 of the slide table 43 can be controlled through operation-of the control panels 23, 24.

Figure 22:
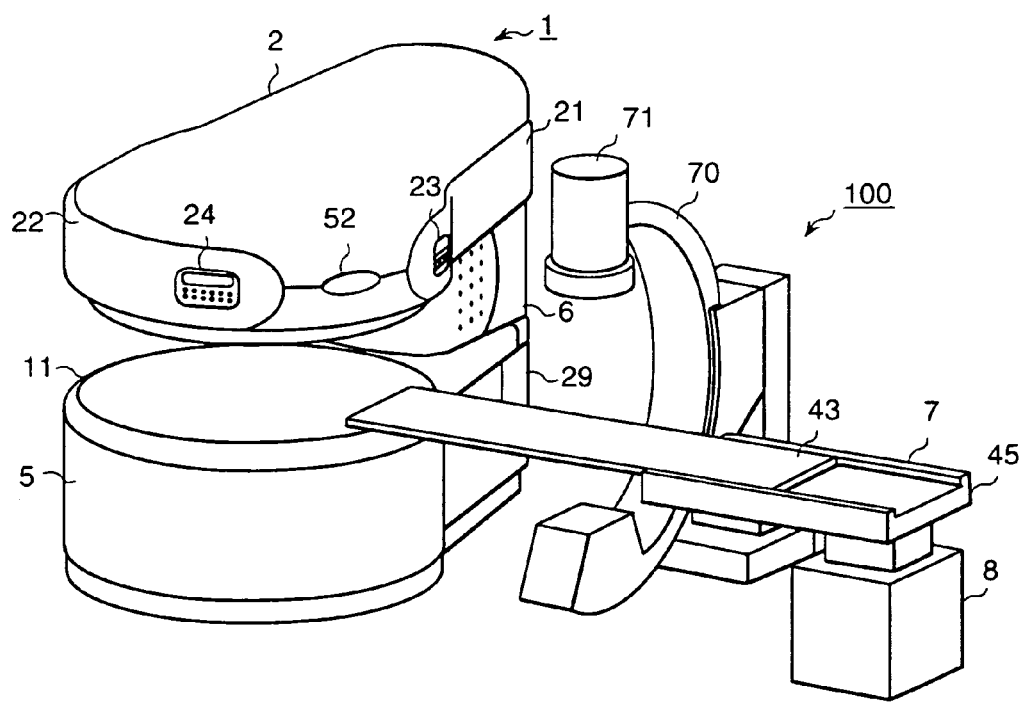
FIG. 22 is a view showing the construction of a diagnosing system.

FIG. 22 and FIG. 23 show an example of a diagnosing system which is constructed by combining any one of the MRI apparatus described above and a C-arm type X-ray equipment as another diagnosing equipment.

The diagnosing system 100 comprises an X-ray imager 71 which is arranged at a position near the table top support of gantry side and straddling the slide table 43, that is, straddling the slide table 43, the mat 44 and the table top 45.

The C-arm type X-ray equipment is suitable as the X-rays imager, and the dotted lines indicate a traveling state when the C-arm type X-ray imager is moved.

By employing such a layout, stepping imaging and porous-chasing imaging at leg artery imaging can be performed using the same slide table 43 used for the MRI imaging. Therefore, the examination can be made speedy, and a burden of transferring the examined person can be reduced.

FIG. 24(1), FIG. 24(2), FIG. 24(3) and FIG. 24(4) show modified examples of the table top support of gantry side 11. The example (1) of FIG. 24(1) is of a quadrilateral type (the setting angle α3 of the bed is about 45 degrees); the example (2) of FIG. 24(2) is of a pentagonal type (the setting angle α3 of the bed is about 72 degrees); the example (3) of FIG. 24(3) is of a hexagonal type (the setting angle α3 of the bed is about 60 degrees); and the example (4) of FIG. 24(4) is of an octagonal type (the setting angle α3 of the bed is about 45 degrees). It can be understood from these examples that the table top support of gantry side is not always necessary to be circular.

Although these examples show the case where the traveling range angle α1 is limited by the column 6, the description of FIG. 1 will be applied in a case where there exist the bridge construction 34, and the setting range of the slide table 43 is limited by the connecting part 30 between the bridge construction 34 and the table top support of gantry side 11.

According to the above-described embodiments, the MRI apparatus comprises a measurement space formed of an upper face of a table top support of gantry side and an under face of a ceiling part; a column arranged in the side face of the measurement space, that is, in one side of the side faces of the table top support of gantry side, the table top support of gantry side and the ceiling part being connected by the column; a main body of apparatus opening to the front side and right hand side and the left hand side with respect to the measurement space; and a bed to be connected to the main body of apparatus.

According to the above-described construction, a doctor and others can approach both sides of the table-top support of gantry side and can more closely approach an examined person because around the table top support of gantry side there are no obstacles preventing the doctor and others from approaching the table top support of gantry side. Therefore, medically dealing with the examined person and medical treatment using medical equipment for the examined person, if necessary, can be performed simultaneously with examination.

Further, since the bed putting the examined person on to be connected to the main body of the apparatus is a separated bed, the bed can be connected to the main body of apparatus from any side, front side or right hand side or left hand side with respect to the measurement space.

Therefore, (1) the configuration that the bed is connected to the main body of the apparatus from the front side of the measurement space, and the doctor and others approach the examined person from both sides in right hand side and left hand side and (2) the configuration that the bed is connected to the main body of the apparatus near the right side or the left side of the column to make a widely open area in the right side or the left side can be made. Accordingly, there are effect that the MRI apparatus can be compactly arranged in a room, and that an open space area required for examination using medical treatment equipments by the doctor and others can be secured.

INDUSTRIAL SUABILITY OF THE PRESENT INVENTION

As having been described above, according to the present invention, since the angle of traveling range capable of setting the slide table support system (for example, the bed 3) having the slide table slidable on the table top support of gantry side can be expanded by a substantial amount, the angle of open space range largely overlapping with the angle of traveling range can be expanded by a substantial amount to make examination or diagnosing work of an examined person easier.

What is claimed is:

1. A nuclear magnetic resonance diagnosing device configured for continuously taking tomograms of an examined person on a bed provided in order to insert the examined person into a space formed between a pair of an upper magnet and a lower magnet, which comprise:
   a cylindrical tabletop support of a gantry side;
   said pair of magnets vertically arranged, said table top support of the gantry side being interposed between said pair of said upper magnet and said lower magnet;
   a column configured for supporting at least said upper magnet; and
   a bridge construction arranged between said column and said table top support of the gantry side, wherein
      said bed comprises a slide table sliding on said tabletop support of the gantry side;

a slide table support means for mounting said slide table in order to be slidable; and a support system having a slide drive unit configured for the slide table, said table top support of the gantry side having a circular side face portion along which said bed is operatively connected so as to be slidably movable along at least a 200° periphery of said circular side face portion, said upper magnet is covered with a top magnet cover and said lower magnet is covered with an examining table body, and first and second connecting parts between said table top support of the gantry side and said bridge construction are placed in quadrants adjacent said support column away from a straight line which passes through a center of said table top support of the gantry side and which crosses at right angles with a straight line passing through the center of said table top support of the gantry side and a center of said support column, said first and second connecting parts forming a portion having a width smaller than a width of said table top support of the gantry side on said straight line crossing at right angles, said table top support of the gantry side further having a contacting surface configured for positioning an extended line in a longitudinal direction of said bed arranged around said table top support of the gantry side so as to pass a center of said table top support of the gantry side, said contacting surface being formed with a circular arc continuously connecting said first and second connecting parts, and at least one control panel of said nuclear magnetic resonance diagnosing device being located on at least one of said upper magnet and said support column.

2. A nuclear magnetic resonance diagnosing device configured for continuously taking tomograms of an examined person on a bed provided in order to insert the examined person into a space formed between a pair of an upper magnet and a lower magnet, which comprises:

a cylindrical tabletop support of a gantry side;

said pair of magnets vertically arranged, said table top support of the gantry side being interposed between said pair of said upper magnet and said lower magnet;

a column configured for supporting at least said magnet arranged in an upper side between said pair of magnets; and a bridge construction arranged between said column and said table top support of the gantry side, wherein said bed comprises a slide table sliding on said tabletop support of the gantry side;

a slide table support means for mounting said slide table in order to be slidable; and a support system having a slide drive unit configured for the slide table, said table top support of the gantry side having a circular side face portion along which said bed is operatively connected so as to be slidably movable along at least a 200° periphery of said circular side face portion, said upper magnet is covered with a top magnet cover and said lower magnet is covered with an examining table body, and first and second connecting parts between said table top support of the gantry side and said bridge construction are placed in quadrants adjacent said support column away from a straight line which passes through a center of said table top support of the gantry side and crosses at right angles with a straight line passing through the center of said table top support of the gantry side and a center of said column, said first and second connecting parts being a portion of which both ends are set back inward from straight lines perpendicular to said orthogonal line and extended toward the support column from points where said orthogonal line crossing at right angles of said table top support of the gantry side and a rim of said table top support of the gantry side intersect each other, and said table top support of the gantry side has a contacting surface configured for positioning an extended line in a longitudinal direction of said bed arranged around said table top support of the gantry side so as to pass a center of said table top support of the gantry side, said contacting surface being formed with a circular arc starting from said first connecting part formed in a quadrant in one side of said column and ending at said second connecting part formed in another quadrant on another side of said column, said bed being arranged opposite to said table top support of the gantry side within an angle formed by said contacting surface, and at least one control panel of said nuclear magnetic resonance diagnosing device being located on at least one of said upper magnet and said support column.

3. A nuclear magnetic resonance diagnosing device configured for continuously taking tomograms of an examined person on a bed provided in order to insert the examined person into a space formed between a pair of an upper magnet and a lower magnet, which comprises:

a cylindrical tabletop support of a gantry side;

said pair of magnets vertically arranged, said table top support of the gantry side being interposed between said pair of said upper magnet and said lower magnet;

a column configured for supporting at least said upper magnet; and a bridge construction arranged between said support column and said tabletop support of the gantry side, which further comprises said bed that comprises a slide table sliding on said tabletop support of the gantry side;

a slide table support means for mounting said slide table in order to be slidable; and a support system having a slide drive unit configured for the slide table, wherein said upper magnet is covered with a top magnet cover and said lower magnet being covered with an examining table body, and first and second connecting parts between said table top support of the gantry side and said bridge construction are placed in quadrants adjacent said support column away from a straight line which passes through a center of said table top support of the gantry side and crosses at right angles with a straight line passing through the center of said table top support of the gantry side and a center of said support column, said first and second connecting parts being portions backed away from a crossing part of a periphery of said table top support of the gantry side and said straight line, into inside of a line extended to said support column at right angles with said straight line, said table top support of the gantry side has a circular side face portion, and said circular side face portion is formed with an angle larger than 200 degrees and smaller than 270 degrees starting from said first connecting part formed in one quadrant adjacent said support column and ending at said second connecting part formed in another quadrant adjacent said support column, said bed being formed and arranged opposite to said table top support of the gantry side within said angle and operatively connected so as to be slidably movable along at least a 200° periphery of said circular side face portion, and at least one control panel of said nuclear magnetic resonance diagnosing device being located on at least one of said upper magnet and said support column.

4. A nuclear magnetic resonance diagnosing device configured for continuously taking tomograms of an examined person on a bed provided to insert the examined person into a space formed between a pair of an upper magnet and a lower magnet, which comprises:

a cylindrical tabletop support of a gantry side;
said pair of magnets vertically arranged, said table top support of the gantry side being interposed between said pair of said upper magnet and said lower magnet;
a column configured for supporting at least said upper magnet; and
a bridge construction arranged between said support column and said table top support of the gantry side, wherein
said bed comprises a slide table sliding on said table top support of the gantry side; a slide table support means for mounting said slide table in order to be slidable; and
a support system having a slide drive unit configured for the slide table, said table top support of the gantry side having a circular side face portion along which said bed is operatively connected so as to be slidably movable at least along a 200° periphery of said circular side face portion, wherein
said upper magnet is covered with a top magnet cover, said lower magnet being covered with an examining table body,
first and second connecting parts between said table top support of the gantry side and said bridge construction are placed in quadrants adjacent said support column away from a straight line which passes through a center of said table top support of the gantry side and crosses at right angles with a straight line passing through the center of said table top support of the gantry side and a center of said support column, said connecting part being backed away from a crossing part of a periphery of said table top support of the gantry side and said straight line, into inside of a line extended to said support column at right angles with said straight line, and
said bed is arranged with an angle of a set range α1 larger than 200 degrees starting from said first connecting part formed in one quadrant adjacent said support column and ending at said second connecting part formed in another quadrant adjacent said column, said bed being arranged opposite to said table top support of the gantry side within the set range α1, and operatively connected so as to be slidably movable along at least a 200° periphery of said circular side face portion, and
at least one control panel of said nuclear magnetic resonance diagnosing device is located on at least one of said upper magnet and said support column.

5. The nuclear magnetic resonance diagnosing device according to claim 4, wherein an end side of said circular side face portion serves as said connecting part.

6. The nuclear magnetic resonance diagnosing device according to claim 1, which further comprises:

a cover configured for covering said upper magnet, said cover having a side cover in a nearly vertical direction, said side cover having the at least one control panel of said nuclear magnetic resonance diagnosing device arranged in one of areas formed by said straight line passing through the center of said table top support of the gantry side and crossing at right angles with said straight line passing through the center of said table top support of the gantry side and a center of said column and by a center line of rotation or having control panels in both of the areas.

7. The nuclear magnetic resonance diagnosing device according to claim 1, which further comprises a drive unit configured for driving said slide table in a horizontal direction and a rotating direction.

8. A diagnosing system comprising a nuclear magnetic resonance diagnosing device according to claim 1, further comprising an X-ray imager being arranged near said tabletop support of the gantry side and vertically to said slide table,
wherein said bed of the nuclear magnetic resonance diagnosing device is movably positionable in order to operatively align with said X-ray imager.

9. The nuclear magnetic resonance diagnosing device according to claim 2, which further comprises:

a cover configured for covering said upper magnet, said cover having a side cover in a nearly vertical direction, said side cover having the at least one control panel of said nuclear magnetic resonance diagnosing device arranged in one of areas formed by said straight line passing through the center of said table top support of the gantry side and crossing at right angles with said straight line passing through the center of said table top support of the gantry side and a center of said column and by a center line of rotation or having control panels in both of the areas.

10. The nuclear magnetic resonance diagnosing device according to claim 3, which further comprises:

a cover configured for covering said upper magnet, said cover having a side cover in a nearly vertical direction, said side cover having the at least one control panel of said nuclear magnetic resonance diagnosing device arranged in one of areas formed by said straight line passing through the center of said table top support of the gantry side and crossing at right angles with said straight line passing through the center of said table top support of the gantry side and a center of said column and by a center line of rotation or having control panels in both of the areas.

11. The nuclear magnetic resonance diagnosing device according to claim 4, which further comprises:

a cover configured for covering said upper magnet, said cover having a side cover in a nearly vertical direction, said side cover having the at least one control panel of said nuclear magnetic resonance diagnosing device arranged in one of areas formed by said straight line passing through the center of said table top support of the gantry side and crossing at right angles with said straight line passing through the center of said table top support of the gantry side and a center of said column and by a center line of rotation or having control panels in both of the areas.

12. The nuclear magnetic resonance diagnosing device according to claim 5, which further comprises:

a cover configured for covering said upper magnet, said cover having a side cover in a nearly vertical direction, said side cover having the at least one control panel of said nuclear magnetic resonance diagnosing device arranged in one of areas formed by said straight line passing through the center of said table top support of the gantry side and crossing at right angles with said straight line passing through the center of said table top support of the gantry side and a center of said column and by a center line of rotation or having control panels in both of the areas.

13. The nuclear magnetic resonance diagnosing device according to claim 2, which further comprises
a drive unit configured for driving said slide table in a horizontal direction and a rotating direction.

14. The nuclear magnetic resonance diagnosing device according to claim 3, which further comprises
a drive unit configured for driving said slide table in a horizontal direction and a rotating direction.

15. The nuclear magnetic resonance diagnosing device according to claim 4, which further comprises
a drive unit configured for driving said slide table in a horizontal direction and a rotating direction.

16. The nuclear magnetic resonance diagnosing device according to claim 5, which further comprises
a drive unit configured for driving said slide table in a horizontal direction and a rotating direction.

17. A diagnosing system comprising a nuclear magnetic resonance diagnosing device according to claim 2, further comprising
an X-ray imager being arranged near said tabletop support of the gantry side and vertically to said table,
wherein said bed of the nuclear magnetic resonance diagnosing device is movably positionable in order to operatively align with said X-ray imager.

18. A diagnosing system comprising a nuclear magnetic resonance diagnosing device according to claim 3, further comprising
an X-ray imager being arranged near said tabletop support of the gantry side and vertically to said slide table,
wherein said bed of the nuclear magnetic resonance diagnosing device is movably positionable in order to operatively align with said X-ray imager.

19. A diagnosing system comprising a nuclear magnetic resonance diagnosing device according to claim 4, further comprising
an X-ray imager being arranged near said tabletop support of the gantry side and vertically to said slide table,
wherein said bed of the nuclear magnetic resonance diagnosing device is movably positionable in order to operatively align with said X-ray imager.

20. A diagnosing system comprising a nuclear magnetic resonance diagnosing device according to claim 5, further comprising
an X-ray imager being arranged near said tabletop support of the gantry side and vertically to said slide table,
wherein said bed of the nuclear magnetic resonance diagnosing device is movably positionable in order to operatively align with said X-ray imager.

* * * * *